United States Patent [19]
Wilson

[11] Patent Number: 5,611,343
[45] Date of Patent: Mar. 18, 1997

[54] HIGH RESOLUTION THREE-DIMENSIONAL ULTRASOUND IMAGING

[75] Inventor: Dennis L. Wilson, Palo Alto, Calif.

[73] Assignee: Loral Aerospace Corp., New York, N.Y.

[21] Appl. No.: 417,090

[22] Filed: Apr. 5, 1995

[51] Int. Cl.⁶ ..................................................... A61B 8/00
[52] U.S. Cl. ............................... 128/660.09; 128/916
[58] Field of Search .......................... 128/660.08–660.09, 128/662.06, 916; 73/618–621

[56] References Cited

U.S. PATENT DOCUMENTS

| | | | |
|---|---|---|---|
| 3,979,711 | 9/1976 | Maginness | 367/87 |
| 4,154,113 | 5/1979 | Engeler | 73/626 |
| 4,222,274 | 9/1980 | Johnson | 73/607 |
| 4,269,066 | 5/1981 | Fischer | 73/639 |
| 4,317,369 | 3/1982 | Johnson | 73/607 |
| 4,434,662 | 3/1984 | Green | 73/641 |
| 4,457,175 | 7/1984 | Ramsay | 73/606 |
| 4,463,608 | 8/1984 | Takeuchi | 73/606 |
| 4,742,829 | 5/1988 | Law | 128/662.05 |
| 4,773,268 | 9/1988 | Inbar | 73/625 |
| 4,817,616 | 4/1989 | Goldstein | 128/662.06 |
| 4,819,650 | 4/1990 | Goldstein | 128/661.01 |
| 4,974,211 | 11/1990 | Corl | 367/7 |
| 4,992,989 | 2/1991 | Watanabe | 367/7 |
| 5,070,879 | 12/1991 | Herres | 128/660.08 |
| 5,088,500 | 2/1992 | Wedel | 128/662.06 |
| 5,113,706 | 5/1992 | Pittaro | 128/661.01 X |
| 5,127,409 | 7/1992 | Daigle | 128/660.07 |
| 5,150,715 | 9/1992 | Ishiguro | 128/662.06 |
| 5,176,142 | 1/1993 | Mason | 128/662.06 |
| 5,181,514 | 1/1993 | Solomon et al. | 128/660.09 |
| 5,211,168 | 5/1993 | Mason | 128/661.01 |
| 5,235,857 | 8/1993 | Anderson | 73/625 |
| 5,269,307 | 12/1993 | Fife | 128/661.01 |
| 5,311,095 | 5/1994 | Smith | 310/334 |
| 5,315,999 | 5/1994 | Kinicki | 128/660.07 |
| 5,318,027 | 6/1994 | Fukui | 128/660.01 |
| 5,320,104 | 6/1994 | Fearnside | 128/661.01 |
| 5,331,947 | 7/1994 | Shturman | 126/4 |
| 5,339,282 | 8/1994 | Kuhn | 367/7 |
| 5,485,839 | 1/1996 | Aida et al. | 128/653.1 |
| 5,492,121 | 2/1996 | Lu | 128/653.1 |

*Primary Examiner*—Francis Jaworski
*Attorney, Agent, or Firm*—K. W. Float; A. W. Karambelas

[57] ABSTRACT

An ultrasound imaging system for generating high resolution, three-dimensional images of the body for medical imaging. The system includes a housing with a rotatable disk at one end having an aperture therein and a plurality of pairs of ultrasonic transducers disposed around the periphery thereof. A flexible member encloses the housing and a fluid filled cavity disposed in the housing in which the transducers are immersed. An ultrasonic transmitter is coupled to the aperture for transmitting ultrasonic energy by way of the aperture, fluid filled cavity and flexible member. A receiver is coupled to the ultrasonic transducers and a processor is coupled to the receiver for sequentially processing reflected ultrasonic energy received by the pairs of ultrasonic transducers to produce a high resolution, three-dimensional image of the body. The system forms a synthetic aperture using the moving ultrasonic transducers. The transducers are moved in a circle, and generate a two inch aperture with resolution that is an order of magnitude better than existing ultrasound devices. Since the transducers move in a circle, the aperture is two inches in two dimensions. Range resolution is generated by a wide bandwidth transmit pulse, and a three-dimensional image is generated that has equal resolution in each of the three dimensions.

11 Claims, 1 Drawing Sheet

HIGH RESOLUTION THREE-DIMENSIONAL ULTRASOUND IMAGING

BACKGROUND

The present invention relates to ultrasound imaging systems, and more particularly, to an ultrasound imaging system for generating a high resolution, three-dimensional image of an object.

Prior art relating to ultrasound imaging of the body is disclosed in the following patents. U.S. Pat. No. 4,992,989 entitled "Ultrasound Probe for Medical Imaging System", U.S. Pat. No. 5,070,879 entitled "Ultrasound Imaging Method and Apparatus", U.S. Pat. No. 5,318,027 entitled "Stack-Connectable Ultrasound Probe, Ultrasound Imaging System and Diagnostic Sonography System", U.S. Pat. No. 5,211,168 entitled "Moving Electrode Transducer for Real Time Ultrasound Imaging for use in Medical Applications", U.S. Pat. No. 5,269,307 entitled "Medical Ultrasonic Imaging System with Dynamic Focusing", U.S. Pat. No. 5,331,947 entitled "Inflatable Sheath for Introduction of Ultrasonic Catheter Through the Lumen of a Fiber Optic Endoscope", U.S. Pat. No. 4,773,268 entitled "Multiple Transducer Ultrasound Probes", U.S. Pat. No. 5,315,999 entitled "Ultrasound Imaging System Having User Preset Modes", U.S. Pat. No. 4,434,662 entitled "Ultrasonic Image Generating Apparatus", U.S. Pat. No. 4,457,175 entitled "Insonification Apparatus for an Ultrasound Transmission System", U.S. Pat. No. 3,979,711 entitled "Ultrasonic Transducer Array and Imaging System", U.S. Pat. No. 5,339,282 entitled "Resolution Enhancement for Ultrasonic Reflection Mode Imaging", U.S. Pat. No. 4,269,066 entitled "Ultrasonic Sensing Apparatus", U.S. Pat. No. 5,176,142 entitled "Endoscopic Ultrasound Probe with Take-up Cable Mechanism", U.S. Pat. No. 5,150,715 entitled "Ultrasound-Imaging Diagnostic System", U.S. Pat. Nos. 4,222,274 and 4,317,369 entitled "Ultrasound Imaging Apparatus and Method", U.S. Pat. No. 5,311,095 entitled "Ultrasonic Transducer Array", U.S. Pat. No. 5,320,104 entitled "Transesophageal Ultrasound Probe", U.S. Pat. No. 4,463,608 entitled "Ultrasound Imaging System", U.S. Pat. No. 4,817,616 entitled "Auto Switch Biplane Prostate Probe", U.S. Pat. No. 5,088,500 entitled "Ultrasound Finger Probe and Method for Use", U.S. Pat. No. 4,742,829 entitled "Intracavitary Ultrasound and Biopsy Probe for Transvaginal Imaging", U.S. Pat. No. 4,819,650 entitled "Biplane Probe Including Centerline Highlighting", and U.S. Pat. No. 4,154,113 entitled "Ultrasonic Imaging System".

A typical ultrasound imaging system is a hand-held phased array that generates a crude image. The imaging system broadcasts short bursts of ultrasonic energy and receives the energy on an array of ultrasound transducers. The transducers are carefully shaped to be wide enough to form a narrow antenna beam in one dimension. In the other dimension, the transducers are treated as a phased array to generate a number of sonic antenna beams forming a crude image of an area of the body. A typical pulse has a bandwidth of 5 megahertz permitting the range resolution to be on the order of 300 microns. However, the resolution in cross range is generally much less, resulting in a blotchy image that is difficult to visualize.

Difficulties that limit the ultrasound imaging system are the narrow pulse used for imaging and the two dimensional image derived from the three-dimensional object that is imaged. The sound absorption in the body tissues is enough that higher frequency sounds are absorbed before they return to the sensor from distant body parts. The use of the imaging system requires the development of user skills regarding interpretation of the images in terms of the anatomy that is imaged and the possible pathologies instead of providing an easy to interpret three-dimensional image.

It has been determined that if the energy pulse that is used to sense the body structure is made longer, the amount of energy that is generated may be made many times larger. With the larger total energy, the problems resulting from energy absorption by the body can be overcome, permitting detailed imaging of deep body parts.

Therefore, it is an objective of the present invention to provide for a three-dimensional ultrasound imaging system that minimized problems caused by energy absorption by the body, thus permitting detailed imaging of deep body parts.

SUMMARY OF THE INVENTION

In order to meet the above and other objectives, the present invention provides for an ultrasonic imaging system that is capable of generating a high resolution, three-dimensional image of an object. The high resolution ultrasonic imaging system employs synthetic aperture concepts and has an order of magnitude better resolution over a particular imaging volume than conventional imaging systems. The ultrasonic imaging system produces high quality images and can be used in place of many X-ray imaging procedures that are currently performed.

The ultrasonic imaging system uses an array of from four to eight ultrasound transducers disposed around the periphery of a rotating disk that are immersed in a bag of fluid, such as water. Optimally, the transducers are spaced at 60 degree intervals around the disk circumference. The transmitter generates a pulse of ultrasonic energy through a hole in the center of the disk that illuminates an object of interest, such as a body that is to be imaged. The ultrasonic energy reflected from the body is received at each of the transducers on the rotatable disk. The transducers are used together to form an image over the three-dimensional volume during rotation of the disk through 120 degrees. Alternatively, the rotation may be through 90 degrees or 180 degrees. The resolution is less if 90 degrees is used, and is not much better than 120 degrees if 180 degrees is used. By spacing sets of transducers at 120 degree increments around the disk, sequences of images are formed, one for each 120 degree rotation of the disk. With a rotation speed of 600 revolutions per minute, the image rate is 30 frames per second.

The concept of a synthetic aperture has been used in the radar art to generate high resolution images derived from an antenna that has a small aperture by moving the antenna. This principal is applied to ultrasound imaging using the present invention to generate high resolution, three-dimensional images of the body for medical imaging purposes. The imaging system has resolution that is an order of magnitude better than currently available ultrasound devices and images a volume instead of a plane.

The basic concept of the present invention is to form a synthetic aperture in the manner performed by a synthetic aperture radar using moving ultrasonic transducers. As in synthetic aperture radars, the resolution of the image increases as the distance through which the transducers move. The transducers are moved in a circle and, for example, generate a two inch aperture with resolution that is an order of magnitude better than existing ultrasound devices. Since the transducers move in a circle, the aperture is two inches in two dimensions.

Range resolution is generated by a wide bandwidth transmit pulse, and a three-dimensional image is generated that has equal resolution in each of the three dimensions, contrasted to the usual ultrasound image where there is good resolution in range, but limited resolution across the image. The present invention generates a very large amount of data and a large amount of computing power is required to generate the images. Schemes are disclosed to reduce the amount of data produced and the required computing power by subsampling the image in range. The subsampled images may be used to preview the images until a particular area of concern is found, whereafter the full resolution image may be generated.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION

Figure 1:
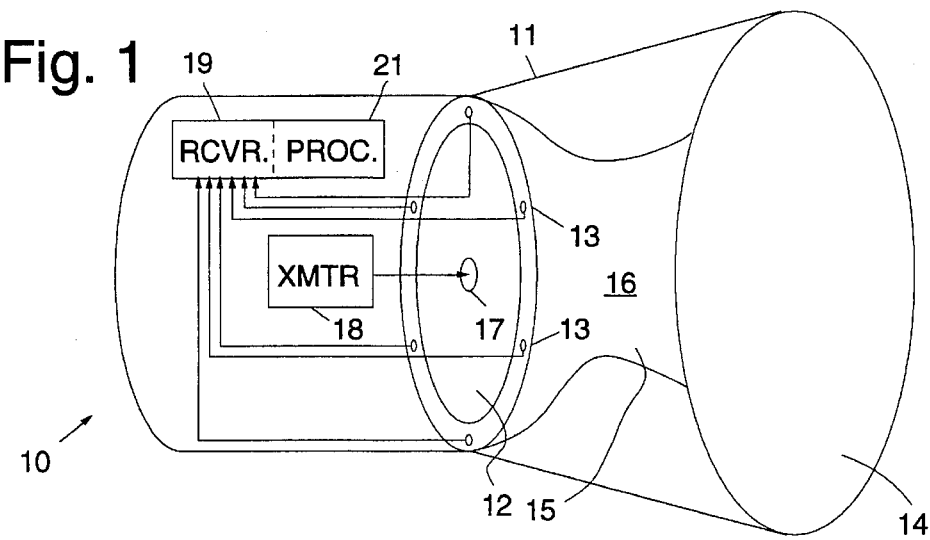
FIG. 1 shows a ultrasonic imaging system in accordance with the principles of the present invention.

Referring to the drawing figures, FIG. 1 shows an ultrasonic imaging system 10 in accordance with the principles of the present invention. It is to be understood that the specific embodiments of the present invention described herein are exemplary of some of the many embodiments contemplated by the present invention. The disclosed embodiments are intended to familiarize the reader with the principles of the present invention and the disclosed embodiments should not be taken as in any way limiting the scope of the present invention.

Figure 2:
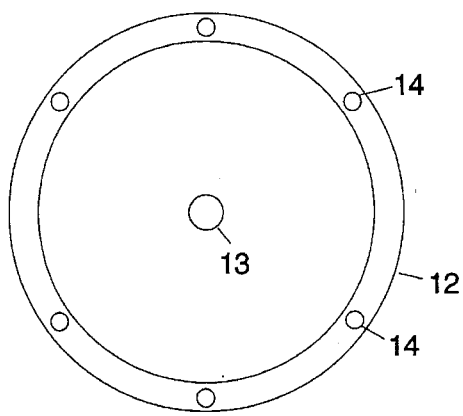
FIG. 2 illustrates the face of a rotatable disk used in the ultrasonic imaging system of FIG. 1.

The ultrasonic imaging system 10 is comprised of a housing 11 that secures a rotatable disk 12 at one end that secures a plurality of pairs of ultrasonic transducers 13 around its periphery and has a flexible face 14 at an opposite end through which ultrasonic energy may be transmitted and received. The ultrasonic imaging system 10 typically uses an array of from four to eight ultrasound transducers 13 disposed around the periphery of the rotatable disk 12. A fluid filled cavity 15, which may contain a fluid 16 such as water, for example, is disposed between the rotatable disk 12 and the flexible face 14. The transducers 13 are typically immersed in the fluid 16 contained in the fluid filled cavity 15. A transmitter aperture 17 is disposed in the center of the rotatable disk 12. An ultrasonic transmitter 18 is coupled to the transmitter aperture 17 and a receiver 19 is coupled to the ultrasonic transducers 13. A processor 21 is coupled to the receiver 19 and is used to process reflected ultrasonic signals derived from the plurality of ultrasonic transducers 13 to produce a high-resolution, three dimensional image. FIG. 2 illustrates the face 14 of the rotatable disk 12 used in the ultrasonic imaging system 10 of FIG. 1 showing the spacing of the transducers 13 around the periphery of the disk 12 and the transmitter aperture 17.

The operation of the ultrasonic imaging system 10 is as follows. The transmitter 18 transmits a pulse of ultrasonic energy through the transmitter aperture 17 in the center of the rotatable disk 12 that illuminates an object, such as a body that is to be imaged. The transmitted ultrasonic pulse ensonifies the area to be imaged. The ultrasonic energy reflected from the body is received at each of the transducers 13 disposed on the rotatable disk 12. Pairs of the transducers 13 are used together to form an image over the three-dimensional volume during the rotation of the disk 12 through 120 degrees. By spacing transducers 13 at 120 degree increments around the disk 12, sequences of images are formed, one for each 120 degree rotation of the disk 12. Alternatively, the rotation of the disk 12 may be through 90 degree increments or 180 degree increments. The resolution is less if a 90 degree increment is used, and is not much better than 120 degrees if a 180 degree increment is used.

Figure 3:
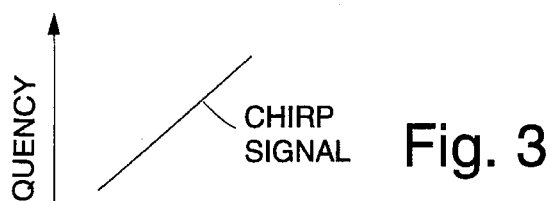
FIG. 3 shows the structure of the transmitted signal from the ultrasonic imaging system, which is a chirp signal with a time-bandwidth product of 1000.

The formation of an image begins with the generation of the pulse of ultrasonic energy from the transmitter. The pulse of energy must illuminate the volume to be imaged, requiring that the transmitter 18 be small in order that the beam pattern from the transmitter 18 cover a large volume. A small transmitter 18 must have its energy spread over a long time in order that the peak energy be small enough to avoid problems with cavitation and other nonlinear effects. The nature of the transmitted waveform is shown in FIG. 3. The transmitted signal is a chirp signal, increasing (or decreasing) in frequency linearly with time. In order to achieve high resolution from the imaging system 10, may transmit a signal that chirps from 2.5 MHz to 7.5 MHz, coveting a bandwidth of 5 MHz. The time bandwidth product of the signal is 1000, yielding a signal duration of 200 microseconds.

The time-bandwidth product of the signal indicates the amount of processing gain that can be realized in establishing the range resolution of the imaging system 10. A gain of 1000 means that the energy that is received can be virtually 1000 times greater than the signal level that is transmitted. The gain of 1000 provides a much higher signal level in the receiver 19 and increases the depth penetration of the sound in light of frequency dependent absorption in the body.

The received signal is the collection of received sounds from each reflector in the body that is imaged. There is a reflected sound from each interface in the body where there is a change in acoustic impedance. The acoustic impedance for a free wave is the speed of sound times the density of the body at that point. There is a reflection whenever there is a change in the density of the body or in the speed of sound. The speed of sound through the body changes little from the speed of sound in water, so most of the reflection is due to a change in density. Such reflections occur whenever there is a change from one type of tissue to another. Such changes occur where there is a vein or artery, where there is connective tissue, and where there is a cavity such as the heart or an abscess.

Figure 4:
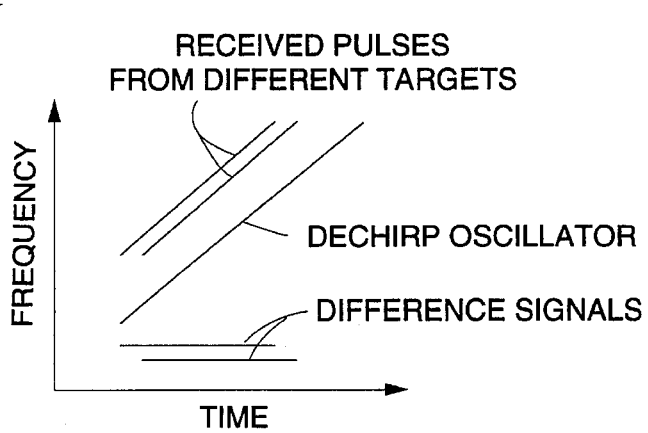
FIG. 4 illustrates the mixing process performed in the processor of the ultrasonic imaging system.

The returned signal is processed in the processor 21 by transforming the signal to form a range dependent signal for each transmitted pulse. The received signal is mixed with a matching chirp signal in a mixer in the receiver 19, resulting in a mixed signal that has a constant frequency for a particular reflector in the body. The range of frequencies from the mixer are processed using a Fourier transform, and in particular a fast Fourier transform (FFT), in the processor 21 to form a signal that has a large amplitude corresponding to the range to the reflection from a point in the body. FIG. 4 illustrates the mixing process that is performed in the processor 21. The received signal is processed for range by de-chirping the signal and then performing a fast Fourier transform on the de-chirped signal.

The next step in processing of the synthetic aperture signal is a polar transformation. The polar transformation changes the coordinates of the pulses from range versus pulse number to range versus angle for two angles in a polar coordinate system 10. The process involves interpolating between the pulse sample values.

The pulses are then processed to form cross range information. In its simplest form, the cross range processing is a two dimensional Fourier transform. The two dimensional Fourier transform effectively forms a virtual beam pattern from the pulses. Since the transmitter 18 is fixed, the received pulses are the same as would have been received by an array of transducers 13 spaced around the circumference of the disk 12 at angles corresponding to the angle turned by the disk 12 between pulses from the transmitter. The circular array of transducers 13 is used to form an image by processing the signals received thereby by means of the two dimensional Fourier transform as discussed above.

In order to shape the response in angle, it is appropriate to weight the responses from virtual array elements (produced by the Fourier transform) depending on the coordinates of the virtual array element with regard to the two dimensions of the Fourier transform. Unweighted, the effective weighting of the transform has a $1/\cos(x)$ form corresponding to the density of virtual receivers projected against the axis of the Fourier transform. A preferred weighting is a Kaiser weighting. The Kaiser weighting is accomplished by first weighting the receivers by $\cos(x)$ to counter the density related virtual weighting and then further weighting by a Kaiser window. Kaiser windows are described in a book entitled "Digital Filter Design" by T. W. Parks and C. S. Burros, Wiley & Sons, New York, 1987 at page 73.

The processing may be made more precise by performing small adjustments to correct errors known as auto-focus adjustment. The Fourier transform is performed for small volumes. The phase of the signal is averaged over the small volume and adjusted to match the phase of other small blocks that image the same area. The effect is one of performing imaging with reduced resolution, adjusting the phase of each of the reduced resolution images, and finishing the processing to form the high resolution image.

The result is an image that has three dimensions, including range and two cross-range dimensions. The range information is provided by the basic chirp operation. The cross range is provided by the two dimensional Fourier transform that generates multiple beams through the volume that is imaged.

The performance achieved by the synthetic aperture ultrasound imaging system 10 may be better understood by way of an example. The parameters of one possible imaging system 10 are as follows. The disk 12 diameter is 50 millimeters (about 2 inches), the rotational speed is 10 revolutions per second (600 RPM), the chirp pulse is from 2.5 to 7.5 MHz, the time-bandwidth product is 1000, the pulse time is 200 microseconds, the pulse rate is 1000 pulses per second, the speed of sound in water is 1500 meters per second, the wavelength at the center frequency is 300 microns, the pulse length is 30 cm (about 1 foot). From the above data it may be determined that the pulse range resolution is 300 microns, the angle of view is +30 degrees, the distance to the viewed volume is 15 cm (about 6 inches), the angular resolution is 0.09 degrees (1.5 milliradians), and the cross range resolution at 300 microns is 20 cm (5 cm inside the body). The result is a three-dimensional view of the imaged volume. The resolution is 300 microns. The frame rate is 30 frames per second. The images are 1024 by 1024 pixels with resolution of 600 by 600 pixels across the image. The volume viewed is roughly a six inch cube.

The volume may be viewed using three-dimensional viewing techniques. By making some densities opaque and others transparent, the structures in the volume may be viewed from any vantage point using well-established view generation algorithms. Alternatively, the images may be presented in slices as are magnetic resonance (MR) or computer tomography (CT) images. Since the images are generated at 30 frames per second, there are very many slices to see.

The processing of the images may include directly measuring the volume of the chambers of a heart. Finding blood vessels is straight forward. The imaging system 10 generates non-invasive, non-radiation producing images of body volumes. The images are generated at an image rate of 30 frames per second. The resolution is very good, permitting a doctor to see fine details of the structure of internal organs.

The amount of data generated is very large, and is generated at a rate 15 to 30 gigabytes per second. The raw data is generated at a rate on the order of 60 megabytes per second. Views may be generated that are 512 by 512 or 1024 by 1024 images for viewing at 30 frames per second. Slices such as those generated by the normal ultrasound imaging may be generated. Another view is a three-dimensional view to see a moving three-dimensional view of the imaged area.

The required processing involves processing 1000 of the 1024 by 1024 two-dimensional FFTs. The result is 2 million 1024 point FFTs to provide for full resolution processing of the image. The computing power required is therefore large if the processing is to be performed quickly. The amount of data generated is also very large. As a result of this, only 10 or 20 of the slices in one dimension are typically generated for preliminary viewing. Further processing may be used to provide a full three-dimensional data set in a restricted volume. For viewing a dynamic three-dimensional image of an organ, such as the heart, reduced sampling in one dimension permits more than adequate visualization of the body part.

An alterative approach to reduce the amount of data is to generate a reduced resolution three-dimensional image. A cube that is 128 by 128 by 128 pixels may be used. These images may be used to provide a preview of the image. When an image of interest is found, the resolution may be increased to full resolution by further processing the data.

Thus there has been described a new and improved ultrasound imaging system for generating a high resolution, three-dimensional image of an object. It is to be understood that the above-described embodiment is merely illustrative of some of the many specific embodiments which represent applications of the principles of the present invention. Clearly, numerous and other arrangements can be readily devised by those skilled in the art without departing from the scope of the invention.

What is claimed is:

1. A synthetic aperture ultrasound imaging system for generating a high resolution, three-dimensional image of an object, said system comprising:

a housing;

a rotatable disk disposed at one end of the housing that has an aperture disposed in its center and that secures a plurality of ultrasonic transducers around the periphery thereof, and wherein the disk and transducers are rotatable about an axis of the disk and form a synthetic aperture when rotated;

a flexible member disposed at a second end of the housing distal from the rotatable disk through which ultrasonic energy may be transmitted and received;

a fluid filled cavity disposed in the housing between the rotatable disk and the flexible member, and wherein the plurality of rotatable ultrasonic transducers are immersed in the fluid of the fluid filled cavity;

an ultrasonic transmitter coupled to the aperture for transmitting ultrasonic energy by way of the aperture, fluid filled cavity and flexible member; and a receiver and processor coupled to the plurality of rotatable ultrasonic transducers for sequentially processing reflected ultrasonic energy received by the plurality of rotatable ultrasonic transducers to produce a high resolution, three-dimensional image of the object.

2. The system of claim 1 wherein the fluid filled cavity contains water.

3. The system of claim 1 wherein the transducers are immersed in the fluid filled cavity.

4. The system of claim 1 wherein the plurality of ultrasonic transducers are disposed around the periphery of the rotatable disk at 120 degree intervals.

5. The system of claim 1 wherein the ultrasonic transducers are angularly separated by 90 degrees.

6. The system of claim 1 wherein the ultrasonic transducers are angularly separated by 180 degrees.

7. A synthetic aperture ultrasound imaging system for generating a high resolution, three-dimensional image of an object, said system comprising:

a housing;

a rotatable disk disposed at one end of the housing that has an aperture disposed in its center and that secures a plurality of ultrasonic transducers around the periphery thereof, and wherein the disk and transducers are rotatable about an axis of the disk and form a synthetic aperture when rotated;

a flexible member disposed at a second end of the housing distal from the rotatable disk through which ultrasonic energy may be transmitted and received;

a fluid filled cavity disposed in the housing between the rotatable disk and the flexible member, and wherein the transducers are immersed in the fluid contained in the fluid filled cavity;

an ultrasonic transmitter coupled to the aperture for transmitting ultrasonic energy by way of the aperture, fluid filled cavity and flexible member; and a receiver and processor coupled to the plurality of ultrasonic transducers for sequentially processing reflected ultrasonic energy received by the plurality of rotatable ultrasonic transducers to produce a high resolution, three-dimensional image of the object.

8. The system of claim 7 wherein the fluid filled cavity contains water.

9. The system of claim 7 wherein the plurality of ultrasonic transducers are disposed around the periphery of the rotatable disk at 120 degree intervals.

10. The system of claim 7 wherein the ultrasonic transducers are angularly separated by 90 degrees.

11. The system of claim 7 wherein the ultrasonic transducers are angularly separated by 180 degrees.

* * * * *